United States Patent [19]

Radulovacki

[11] Patent Number: 4,537,907

[45] Date of Patent: Aug. 27, 1985

[54] HYPNOTIC COMPOSITION AND METHOD OF INDUCING SLEEP

[75] Inventor: Miodrag Radulovacki, Evanston, Ill.

[73] Assignee: University of Illinois Foundation, Urbana, Ill.

[21] Appl. No.: 194,662

[22] Filed: Oct. 6, 1980

[51] Int. Cl.³ .......................................... A61K 31/195
[52] U.S. Cl. .................................................... 514/567
[58] Field of Search ........................................ 424/319

[56] References Cited

U.S. PATENT DOCUMENTS 4,073,929  2/1978  Callery et al. .
4,180,509  12/1979  Metcalf et al. .

OTHER PUBLICATIONS

Hartmann, Waking and Sleeping, (1977), 1:155-161-"-L-Tryptophane as a Hypnotic Agent: A Review".
Chemical Abstracts 76: 107920w (1972).
Chemical Abstracts 92: 15551d (1-30-80).

Primary Examiner—Jerome D. Goldberg
Attorney, Agent, or Firm—Marshall, O'Toole, Gerstein, Murray & Bicknell

[57] ABSTRACT

A hypnotic composition and method of inducing sleep in a mammal by administering to a mammal in a pharmaceutical carrier a hypnotically effective dose of a salt of 2-amino-3-(1-naphthyl) propanoic acid in the form of an injectable solution, capsule tablet or syrup.

3 Claims, No Drawings

HYPNOTIC COMPOSITION AND METHOD OF INDUCING SLEEP

This inventon relates generally to hypnotic compositions and more particularly to naphthyl substituted amino propanoic acid compositions which have been found useful for hastening slow wave sleep and postponing the wakening time.

Heretofore, physiological activity has been found in aromatic substituted amino propanoic acid compounds, such as L-tryptophan (i.e. alpha-amino-beta-indole-propanoic acid). It is impossible, however, for one skilled in the art to predict with any degree of accuracy the physiological behavior of amino-propanoic acid compounds having as a substituent a markedly different aromatic group.

The aromatic substituted amino-propanoic acid compositions which exhibit significant hypnotic activity comprise (2-amino-3-naphthyl)propanoic acid compounds and non-toxic salts thereof, such as 2-amino-3-(1-naphthyl)propanoic acid which has the following structural formula:

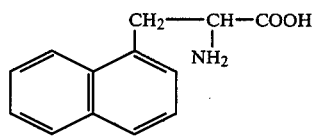

The compound 2-amino-3-(1-naphthyl)propanoic acid can be synthesized according to the method of H. Erlenmeyer et al (Helv. chim. Acta, 30: 297-394, 1947) and comprises pouring 12 cc of concentrated hydrochloric acid over 1.5 g of 1-(naphthyl methyl)alpha-amino malonic acid in a glass stoppered flask and cautiously heated the flask in an oil bath. This causes intially marked foaming. After heating 10 minutes a perfectly clear solution is formed. On continuing quiet boiling for about 20 minutes the hydrochloride of the desired amino acid product begins to precipitate. Sufficient heating to effect quiet boiling was continued for 2 hours. Thereafter, the mass was transferred to a large porcelain evaporating dish and evaporated in a water bath to dryness. This reaction yields 1.25 g of a nearly white powder substance corresponding to alpha-amino-β[naphthyl-(1)]-propanoic acid. This crude preparation is further purified by recrystallizing the compound from water or by dissolving in hot alcohol and precipitating from the cooled solution with ether.

Acids useful for preparing acid-addition salts in the invention include, among others, inorganic acids such as hydrochloric, hydrobromic, sulfuric, and phosphoric acids, and organic acids such as maleic, fumaric, tartaric, citric, 2-acetoxybenzoic, salicylic, succinic, or methane-sulfonic acids.

The physiological effects of the compositions of the present invention on sleep states were studied by administering the compound (2-amino-3-(1-naphthyl)-propanoic acid hydrochloride (HCl) to adult male Sprague-Dawley rats weighing about 400–500 grams in which electrodes for electroencephalograms (EEG) and electromyograms (EMG) were implanted. The implantation procedure was carried out under pentobarbital anesthesia (40 mg/kg.IP) with supplemental administration of ether as required. Atropine methyl nitrate (2 mg/kg,SC) was also given to eliminate bronchial congestion during surgery. Surgery involved bilateral implanation of two stainless steel screw electrodes (size 0-80×⅛ inch) into the parietal bones and insertion of two paddle-shaped wire electrodes into the dorsal neck muscles. All electrodes were soldered to the appropriate leads of a connector which was fixed to the skull by dental cement. Two additional stainless steel screws were inserted, one into the occipital bone and the other into the frontal bone, to help anchor the implant. Prior to suturing each animal, Neosporin (each gram contains polymyxin B sulfate, 5,000 units, bicitracin zinc 400 units, and neomycin sulfate 5 mg) ointment was topically applied to the incision site. All animals then received an injection of Bicillin (pencillin G benzathine and penicillin G procaine in aqueous suspension) 150,000 units (SC) and were allowed a minimum of one week recovery.

At 10:00 a.m. on the day of the experiment, the animals received either saline (4 ml/kg, IP) or DL 2-amino-3-(1-naphthyl)propanoic acid HCl (30 mg/kg) IP dissolved in saline at a concentration of 7.5 mg/ml, pH 6.0) and were polygraphically recorded until 4:00 p.m. No more than eight animals were recorded at one time on two Grass-VIII channel electroencephalographs. Prior to each recording session, all animals were acclimated to the recording unit and cable for 2 days. Evaluations of the polygraphic records were made using standard techniques where each epoch of record was determined to be either wakefulness (W), slow wave sleep (SWS) or rapid eye movement(REM) sleep. The epochs were one minute long and the speed of the paper drive was two minutes per page (2.5 mm/second). Behavioral observations via closed circuit television were noted on the EEG recorded during the experiment. The amount of time spent in either W, SWS or REM sleep was calculated at half-hour intervals for the first hour and at one hour intervals for the entire 6-hour recording session. The effects of 2-amino-3-(1-naphthyl)propanoic acid hydrochloride on the sleep-wake pattern was assessed using the Student t-test in which the amount of time spent in each of the three behavioral states during the various time intervals was compared to the control.

In addition, SWS and REM sleep latencies (time between injection and the appearance of the first two minute SWS or the first one minute REM sleep episode) were determined. The Student t-test was used to determine significance between control and experimental latencies.

The effects of 2-amino-3-(1-naphthyl)propanoic acid on the time of occurrence of the first slowwave sleep (SWS) and the first rapid eye movement (REM) sleep (i.e. sleep latencies) are shown in the following Table 1:

TABLE 1

EFFECTS OF 2-Amino-3-(1-Naphthyl) Propanoic ACID HCl, 30 mg/kg, IP, ON LATENCIES TO FIRST SWS AND FIRST REM SLEEP EPISODES IN RATS

|  | Control | Experimental |
| --- | --- | --- |
| SWS Latency | 40 ± 4 | 25 ± 2* |
| REM Sleep Latency | 70 ± 5 | 58 ± 7 |

The results are expressed as means ±SE (minutes) for 14 control and 7 Experimental animals.
*p < 0.02 by Student t-test.

It can be seen that the administration of this agent reduced SWS latency from 40±5 min. in the control group to 25±5 min. in the experimental group ($p<0.02$). This represents a 37% decrease from the controls. The latency to the first REM sleep episode following administration of the agent changed from $70\pm5$ in the controls to $58\pm7$ in the experimental group.

The effects of 2-amino-3-(1-naphthyl) on the sleep states of wakefulness (W), slowwave sleep (SWS) and rapid eye movement (REM) sleep are shown in the following Table 2:

TABLE 2
EFFECTS OF 2-Amino-3-(1-Naphtyl) Propanoic Acid HCl, 30 mg/kg, IP, ON W, SWS AND REM SLEEP STATES IN RATS

| Time Interval (Hr) | W Control | W Expmt. | SWS Control | SWS Expmt. | REM Control | REM Expmt. |
|---|---|---|---|---|---|---|
| 0.0–0.5 | 29 ± 1 | 25 ± 1# | 1 ± 1 | 5 ± 1# | 0 | 0 |
| 0.5–1.0 | 17 ± 2 | 12 ± 4 | 12 ± 2 | 17 ± 4 | 1 ± 0 | 1 ± 1 |
| 0–1 | 46 ± 3 | 36 ± 5 | 13 ± 2 | 22 ± 4* | 1 ± 0 | 1 ± 1 |
| 1–2 | 11 ± 1 | 20 ± 3++ | 42 ± 1 | 35 ± 3+ | 7 ± 1 | 5 ± 1 |
| 2–3 | 17 ± 4 | 9 ± 2 | 37 ± 4 | 43 ± 2 | 6 ± 1 | 8 ± 1 |
| 3–4 | 28 ± 4 | 17 ± 3 | 29 ± 3 | 38 ± 3 | 3 ± 1 | 5 ± 1 |
| 4–5 | 22 ± 4 | 20 ± 5 | 33 ± 4 | 33 ± 4 | 5 ± 1 | 6 ± 2 |
| 5–6 | 17 ± 5 | 10 ± 4 | 37 ± 4 | 43 ± 4 | 7 ± 1 | 7 ± 1 |
| 0–6 | 141 ± 8 | 112 ± 8* | 190 ± 6 | 215 ± 2* | 28 ± 4 | 33 ± 4 |

The results are expressed as means ±SE (minutes) for 14 control and 7 Experimental animals.
$p < 0.002$
+$p < 0.02$
*$p < 0.5$
++$p < 0.005$ The data of Table 2 are presented in one hour intervals for the entire 6-hour recording period. In addition, the first hour of the recording is subdivided into two consecutive half-hour periods in order to correlate the initial effects of the drug on sleep with its effects on brain chemistry. It can be seen that the administration of 2-amino-3-(1-naphthyl)propanoic acid HCl reciprocally enhanced SWS ($p<0.002$) and reduced waking time ($p<0.002$) by 4 min. during the first half-hour period of EEG recording. This increase in SWS time coincided with the reduction found in SWS latency. During the second half-hour period, there was a tendency toward an increase in SWS and a decrease in W. However, this was not statistically significant. Statistical analysis performed at one-hour intervals showed that 2-amino-3-(1-naphthyl)propanoic acid HCl increased SWS by 9 min. ($p<0.05$) during the first hour with no change in W or REM sleep. However, during the second hour of EEG recording, SWS time was reduced by 7 min. ($p<0.02$) and W was increased by 9 min. ($p<0.005$). There were no changes in either W, SWS or REM sleep for the remaining four hours of the recording session. The overall behavioral effect of 2-amino-3-(1-naphthyl)-propanoic acid HCl as monitored by the EEG for 6 hours was an increase in SWS by 25 min., a decrease in W by 29 min. and no change in REM sleep.

The compositions of the present invention and the water solubles non-toxic salts, such as the hydrochloride, are useful as a hypnotic in several pharmacological forms, including sterile solutions for interperitoneal, intramuscular, subcutaneous or intravenous injections, either alone or in combination with other therapeutic agents, and orally in the form of capsules or tables or as a suppository. The compound 2-amino-3-(1-naphthyl)-propanoic acid and its salts can be compounded by the usual pharmaceutical methods for use as a hypnotic agent for inducing sleep. Dosage units for the hypnotic compositions of the present invention can vary from about 0.05 to about 100 mg per kg per day. Normal dosage units for oral administration will vary from about 10 to about 500 mg per kg per day. For oral administration to humans the dosage range can be from about 0.1 to about 5 grams per day, preferably from about 0.5 to about 2.5 grams per day.

Typical useful pharmaceutical formulations suitable for injection are illustrated in the following specific examples:

EXAMPLE 1

| | | |
|---|---|---|
| 2-Amino-3-(1-naphthyl) propanoic acid hydrochloride | percent | 1.0 |
| Methocel | percent | 4.0 |
| Propylene glycol | percent | 20.0 |
| Distilled water | percent | q.s. |

EXAMPLE 2

| | | |
|---|---|---|
| 2-Amino-3-(1-naphthyl) propanoic acid hydrochloride | percent | 1.0 |
| Benzyl alcohol | percent | 0.9 |
| Water for injection | percent | q.s |

The active agent of this invention can be incorporated with excipients so that an oral dosage will be obtained suitable for use in the form of capsule tablets, troches, elixirs, suspensions, syrups, wafers, chewing gums, and the like. The tablets, troches, pills, capsules and the like will generally contain the following: a binder such as gum tragacanth, acacia, corn starch or gelatin; and excipients such as dicalcium phosphate; a disintegrating agent such as corn starch, potato starch, alginic acid and the like; a lubricant such as mangesium stearate; and a sweetening agent such as sucrose, fructose, lactose or saccharin can be added or a flavoring agent such as peppermint, oil of wintergreen, or cherry flavoring. The tablets, pills or capsules can be coated with shellac, sugar, or both. A syrup or elixir can contain the active compounds, sucrose as a sweetening agent, methyl and propyl parabens as a preservatives, a dye and a flavoring agent, such as cherry or orange flavor. The materials used in preparing any dosage unit form should be pharmaceutically pure and substantially non-toxic in the amounts employed.

Formulations of the active ingredients which are suitable for oral administration are illustrated by the following specific examples:

EXAMPLE 3

PREPARATION OF CAPSULE FORMULATION

| Ingredient | Milligrams per Capsule |
| --- | --- |
| 2-amino-3-(1-naphthyl) propanoic acid hydrochloride | 500 |
| Starch | 180 |
| Magnesium stearate | 10 |

The active ingredient, starch and magnesium stearate are blended together. The mixture is used to fill hard shell capsules of a suitable size at a full weight of 690 milligrams per capsule.

EXAMPLE 4

PREPARATION OF TABLET FORMULATION

| Ingredient | Milligrams per Tablet |
| --- | --- |
| 2-amino-3-(1-naphthyl) propanoic acid hydrochloride | 1000 |
| Lactose | 2000 |
| Corn starch (for mix) | 500 |
| Corn starch (for paste) | 500 |
| Magnesium stearate | 50 |

The active ingredient, lactose and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° F. The dry granules are passed through a No. 16 screen. The mixture is lubricated with magnesium stearate and compressed into tablets in a suitable tableting machine. Each tablet contains 1000 milligrams of active ingredient.

EXAMPLE 5

PREPARATION OF ORAL SYRUP FORMULATION

| Ingredient | Amount |
| --- | --- |
| 2-amino-3-(1-naphthyl) propanoic acid hydrochloride | 100 mg |
| Sorbitol solution (70% N.F.) | 50 ml |
| Sodium benzoate | 150 mg |
| Sucaryl | 90 mg |
| Saccharin | 10 mg |
| Orange flavor | 50 mg |
| Distilled water q.s. to | 100 ml |

The sorbitol solution is added to 50 milliliters of water and the active ingredient is suspended therein. The sucaryl, saccharin, sodium benzoate, flavor and dye are added and dissolved in the above solution. The volume is adjusted to 100 milliliters with distilled water.

In the above formulation, a suspending agent such as bentonite magma, tragacanth, carboxymethylcellulose, or methylcellulose can be used in place of sorbitol. Phosphates, citrates or tartarates can be added as buffers. Preservatives may include the parabens, sorbic acid and the like in place of sodium benzoate and other flavors and dyes can be used in place of those listed above.

While the biological mechanism by which the 2-amino-3-(1-naphthyl)propanoic acid compound produces a marked hypnotic effect by significantly decreasing the slow wave sleep latency and increasing the slow wave sleep time has not been definitely determined and the invention is not dependent on any theory of action, it is possible the mechanism involves the 2-amino-3-(1-naphthyl)propanoic acid compound acting as a 5-hydroxytryptamine (5-HT) agonist and stimulating 5-HT receptors, a condition which has been associated with the sleep state. Also, the synthetic amino acid 2-amino-3-(1-naphthyl)propanoic acid or a metabolite thereof may compete with the natural amino acids tyrosine and tryptophan for uptake into the brain and thereby decreasing the availability of the natural amino acids in the brain and decreasing the synthesis of brain monoamines, such as catecholamine, reduced amounts of which have been associated with the sleep state.

I claim:

1. A method of providing hypnotic therapy to a mammal comprising, administering to said mammal a hypnotically effective amount of a compound selected from the group consisting of 2-amino-3-(naphthyl)propanoic acid and its pharmaceutically acceptable salts in a pharmaceutically acceptable carrier therefor.

2. A method as in claim 1, wherein said compound is selected from the group consisting of 2-amino-3-(1-naphthyl)propanoic acid and its pharmaceutically acceptable salts.

3. A method as in claim 1, wherein said compound is 2-amino-3-(1-naphthyl)propanoic acid hydrochloride.

* * * * *